(12) United States Patent
Ausburn

(10) Patent No.: US 9,818,569 B2
(45) Date of Patent: Nov. 14, 2017

(54) HIGH DOSE OUTPUT, THROUGH TRANSMISSION TARGET X-RAY SYSTEM AND METHODS OF USE

(71) Applicant: Rad Source Technologies, Inc., Suwanee, GA (US)

(72) Inventor: Phillip Kent Ausburn, Cumming, GA (US)

(73) Assignee: RAD SOURCE TECHNOLOGIES, INC, Buford, GA (US)

( * ) Notice: Subject to any disclaimer, the term of this patent is extended or adjusted under 35 U.S.C. 154(b) by 392 days.

(21) Appl. No.: 14/587,634

(22) Filed: Dec. 31, 2014

(65) Prior Publication Data
US 2016/0189911 A1    Jun. 30, 2016

(51) Int. Cl.
*H01J 35/32*    (2006.01)
*H01J 35/18*    (2006.01)
(Continued)

(52) U.S. Cl.
CPC .............. *H01J 19/32* (2013.01); *H01J 1/16* (2013.01); *H01J 1/40* (2013.01); *H01J 19/48* (2013.01);
(Continued)

(58) Field of Classification Search
CPC ........... A61B 6/00; A61B 6/40; A61B 6/4035; A61B 6/4042; A61B 6/4064; A61B 6/44; A61B 6/48; A61B 6/482; A61N 5/1077; G21K 1/00; G21K 2201/00; G21K 2223/00; G21K 2223/20; G21K 2223/204; G21K 2223/206; G21K 2223/313; G21K 2223/317; G21K 2223/40; H05G 1/00; H05G 1/02; H01J 1/00; H01J 1/02; H01J 1/13; H01J 1/15; H01J 1/16; H01J 1/36; H01J 1/38; H01J 1/40; H01J 1/88; H01J 1/94; H01J 3/00; H01J 3/08; H01J 3/10; H01J 3/12; H01J 5/02; H01J 5/04; H01J 5/08; H01J 5/10; H01J 5/18; H01J 19/00; H01J 19/02; H01J 19/10; H01J 19/28; H01J 19/32; H01J 19/34; H01J 19/42; H01J 19/48; H01J 19/54; H01J 19/56; H01J 19/57; H01J 33/00; H01J 33/02; H01J 33/04; H01J 35/00; H01J 35/02;
(Continued)

(56) References Cited

U.S. PATENT DOCUMENTS 5,090,043 A * 2/1992 Parker .................. A61N 5/1001
378/121
5,504,799 A * 4/1996 Suzuki .................... H01J 35/02
378/121
(Continued)

*Primary Examiner* — Anastasia Midkiff
(74) *Attorney, Agent, or Firm* — Jeffrey Watson; Matthew Grell; Grell & Watson Patent Attorneys LLC

(57) ABSTRACT

A high dose output, through transmission target X-ray tube and methods of use includes, in general an X-ray tube for accelerating electrons under a high voltage potential having an evacuated high voltage housing, a hemispherical shaped through transmission target anode disposed in said housing, a cathode structure to deflect the electrons toward the hemispherical anode disposed in said housing, a filament located in the geometric center of the anode hemisphere disposed in said housing, a power supply connected to said cathode to provide accelerating voltage to the electrons.

20 Claims, 10 Drawing Sheets

(51) Int. Cl.
*H01J 35/08* (2006.01)
*H01J 37/06* (2006.01)
*H01J 19/32* (2006.01)
*H01J 19/48* (2006.01)
*H01J 1/16* (2006.01)
*H01J 1/40* (2006.01)
*H01J 37/063* (2006.01)
*H01J 35/06* (2006.01)
*H01J 35/16* (2006.01)
*H01J 1/94* (2006.01)
*A61B 6/00* (2006.01)
*H01J 19/57* (2006.01)

(52) U.S. Cl.
CPC .............. *H01J 35/08* (2013.01); *H01J 35/18* (2013.01); *H01J 35/32* (2013.01); *H01J 37/063* (2013.01); *A61B 6/40* (2013.01); *A61B 6/482* (2013.01); *H01J 1/94* (2013.01); *H01J 19/57* (2013.01); *H01J 35/06* (2013.01); *H01J 35/16* (2013.01); *H01J 2235/087* (2013.01); *H01J 2235/186* (2013.01); *H01J 2893/0006* (2013.01); *H01J 2893/0012* (2013.01)

(58) Field of Classification Search
CPC .. H01J 35/04; H01J 35/06; H01J 35/08; H01J 35/108; H01J 35/16; H01J 35/18; H01J 35/32; H01J 37/00; H01J 37/02; H01J 37/04; H01J 37/06; H01J 37/063; H01J 37/147; H01J 37/1471; H01J 37/1473; H01J 37/16; H01J 2235/00; H01J 2235/06; H01J 2235/08; H01J 2235/081; H01J 2235/083; H01J 2235/086–2235/088; H01J 2235/16; H01J 2235/18; H01J 2235/186; H01J 2893/00; H01J 2893/0001–2893/0006; H01J 2893/0009; H01J 2893/0012; H01J 2893/0019; H01J 2893/002; H01J 2893/0021

See application file for complete search history.

(56) References Cited

U.S. PATENT DOCUMENTS

| | | | | |
|---|---|---|---|---|
| 5,621,780 | A * | 4/1997 | Smith | A61N 5/1001 378/119 |
| 5,729,583 | A * | 3/1998 | Tang | A61B 6/145 378/122 |
| 6,324,257 | B1 * | 11/2001 | Halavee | A61N 5/1001 378/121 |
| 6,493,419 | B1 * | 12/2002 | Dinsmore | A61N 5/1001 378/121 |
| 7,158,612 | B2 * | 1/2007 | Rusch | H01J 35/08 378/121 |
| 7,965,818 | B2 * | 6/2011 | Jaafar | H01J 35/065 378/121 |
| 8,295,440 | B2 * | 10/2012 | Cho | H01J 35/06 378/122 |
| 9,484,177 | B2 * | 11/2016 | Ausburn | H01J 35/06 |
| 2013/0003931 | A1 * | 1/2013 | Funk | A61N 5/1014 378/65 |
| 2014/0369469 | A1 * | 12/2014 | Ogura | H01J 35/08 378/62 |

\* cited by examiner

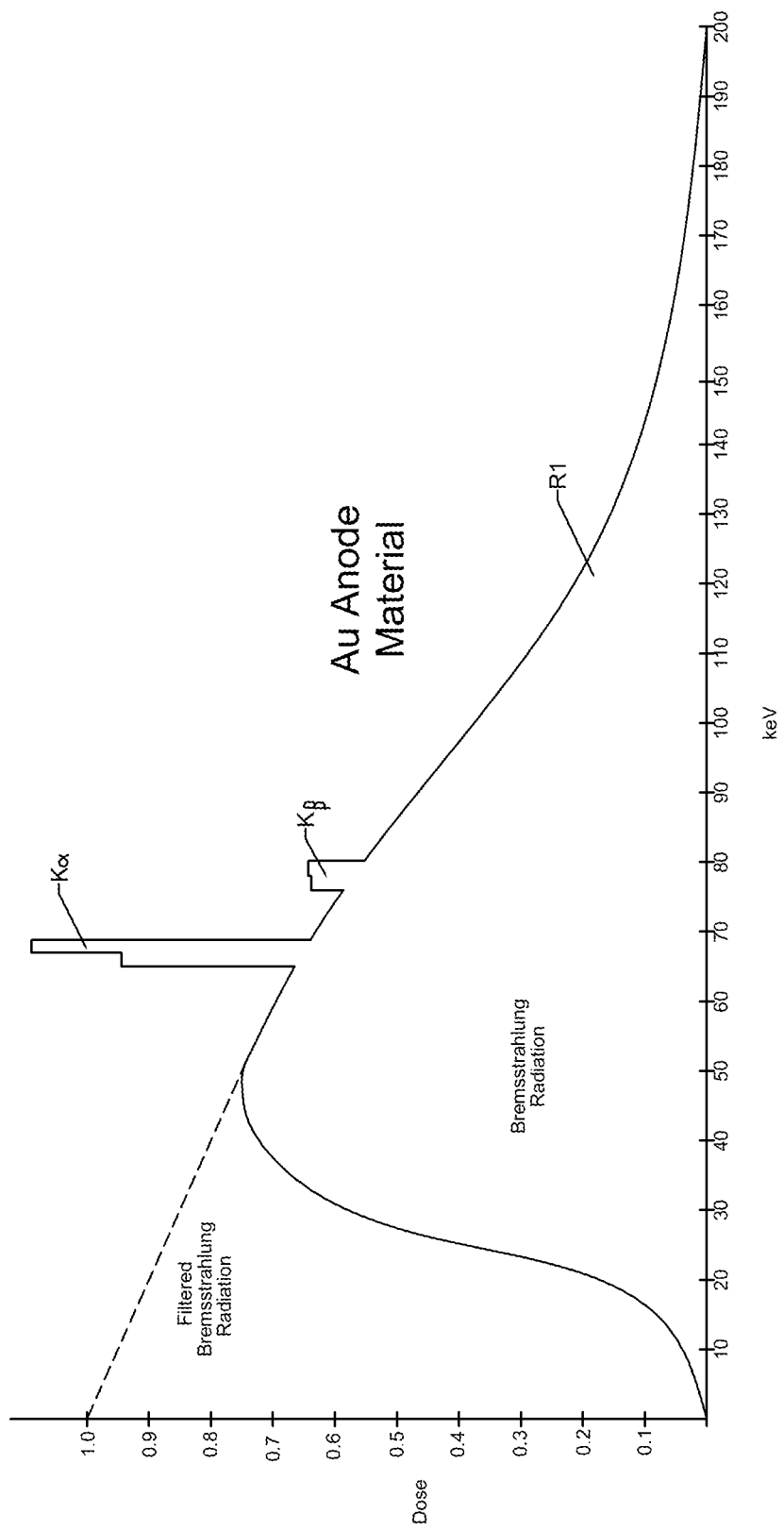

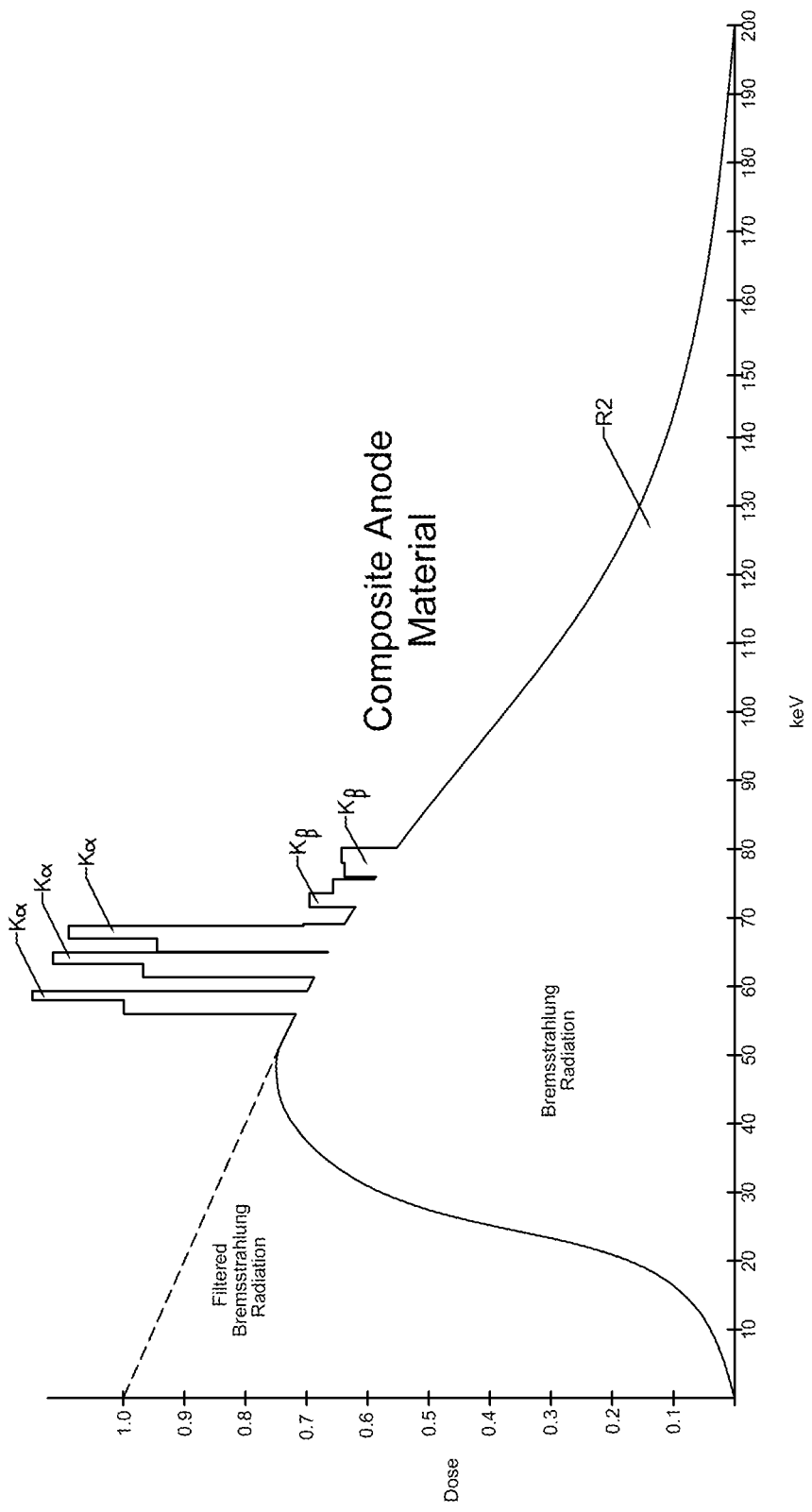
Fig. 3.1

HIGH DOSE OUTPUT, THROUGH TRANSMISSION TARGET X-RAY SYSTEM AND METHODS OF USE

TECHNICAL FIELD

The disclosure relates generally to X-ray tube technology and more specifically it relates to X-ray tubes with specific anode, cathode, filament configurations and material choices to produce high dose X-ray output.

BACKGROUND

In many typical state of the art X-ray tubes, a cathode assembly and an anode assembly are vacuum sealed in a glass or metal envelope. Electrons are generated by at least one cathode filament in the cathode assembly. These electrons are accelerated toward the anode assembly by a high voltage electrical field. The high energy electrons generate X-rays upon impact with the anode assembly. A by-product of this process is the generation of substantial amounts of heat.

Traditional X-ray tube configurations are known in the prior art, for example, Coolidge type X-ray tubes. In a Coolidge tube X-ray photons, shown as a spot output radiation pattern, are generated by impinging an electron beam emanating from filament onto the surface of a target anode. Coolidge tubes may be operated single ended with the cathode at a negative potential and the anode at ground, or double ended with the cathode at a negative potential and the anode at a positive potential. In either configuration the energy of acceleration is the difference between the electrode potentials. In a Coolidge X-ray tube the target anode is fabricated from a heavy metal such as tungsten, tantalum or iridium and such materials are selected because of their density and high melting point. The material of the target anode is most often mounted onto a thermally conductive material such as copper and is externally cooled either by water or dielectric oil.

The target anode is placed in line with the electron beam and radiation is emitted at right angles to the electron beam. The spectrum of the output radiation is predominantly bremsstrahlung and is altered by changing the accelerating energy of the electron beam. Tubes of this nature are use in industrial imaging, medical imaging, analytical and irradiation application. The primary limitation of this type of tube is the watt density loading of the target anode before melting occurs, limited utilization of generated X-ray photons and the symmetry of the resulting radiation field. Because the resolution of an imaging device, either electronic or film, is a function of the size of the electron beam projected onto the target anode. For optimal image resolution a small focal spot is desired, but for optimal image contrast a large number of X-ray photons are desired. The two requirements are contrary and cannot be resolved in the traditional tube design. In addition the reflective nature of the emitted radiation is asymmetrical about a beam centerline and is grossly inefficient for X-ray irradiation applications.

Recently, some low power through transmission X-ray tubes have become available on the market. These tubes use a use a single element as a combination target and output window. Most often the element used is Tungsten because of its higher melting point but at the expense of a reduction in radiation output.

Therefore, it is readily apparent that there is a recognizable unmet need for a high dose output, through transmission target X-ray system and methods of use, having a large surface area anode target to dissipate heat, and thus, enabling a higher atomic number target material with improved radiation output, lower melting point and higher vaporization pressure, and low electrode potential required to produce higher output radiation.

BRIEF SUMMARY

Briefly described, in example embodiment, the present apparatus overcomes the above-mentioned disadvantage, and meets the recognized need for a high dose output, through transmission target X-ray tube and methods of use including, in general, an X-ray tube for accelerating electrons under a high voltage potential, said X-ray tube includes an evacuated housing that is sealed, a through transmission target anode structure disposed on said housing, said anode structure configured in a hemispherical shape having a geometric center, a cathode structure disposed in said housing, said cathode configured to deflect the electrons toward said hemispherical anode, a filament disposed in said housing, said filament positioned proximate said geometric center of said hemispherical shape and between said anode and said cathode, an evacuated housing, said housing configured to vacuum seal there in said anode, said cathode, and said filament, and, thus, such X-ray tube functions to provide a large surface area anode target to dissipate heat and to enable use of different z materials to take advantage of the characteristic X-ray with improved radiation output, lower melting point, and lower electrode potential required to produce higher output radiation.

According to its major aspects and broadly stated, the a high dose output, through transmission target X-ray tube and methods of use includes, in general an X-ray tube for accelerating electrons under a high voltage potential having an evacuated high voltage housing, a hemispherical shaped through transmission target anode disposed in said housing, a cathode structure to deflect the electrons toward the hemispherical anode disposed in said housing, a filament located in the geometric center of the anode hemisphere disposed in said housing, a power supply connected to said cathode to provide accelerating voltage to the electrons.

In an exemplary embodiment of through transmission target X-ray tube and methods of use, the X-ray tube including an evacuated housing that is sealed, a through transmission target anode structure disposed on the housing, the anode structure configured in a hemispherical shape having a geometric center, a cathode structure disposed in the housing, the cathode configured to deflect the electrons toward the anode structure, a filament disposed in the housing, the filament positioned proximate the geometric center of the hemispherical shape and between the anode and the cathode, wherein the evacuated housing is configured to vacuum seal therein the anode structure, the cathode structure, and the filament.

Accordingly, a feature of the high dose output, through transmission target X-ray tube and methods of use is its ability to generate symmetrical X-ray field.

Another feature of the high dose output, through transmission target X-ray tube and methods of use is its ability to provide large surface area anode target to dissipate heat.

Still another feature of the high dose output, through transmission target X-ray tube and methods of use is its ability to enable use of a different z material to take advantage of the characteristic X-ray which will increase radiation output.

Still another feature of the high dose output, through transmission target X-ray tube and methods of use is its ability to use target materials with lower melting points for specialized applications such as the generation of monochromatic X-rays and for therapeutic applications.

Still another feature of the high dose output, through transmission target X-ray tube and methods of use is its ability to utilize a lower electrode potential to produce higher output radiation.

Yet another feature of the high dose output, through transmission target X-ray tube and methods of use is its ability to provide a new anode configuration which makes possible the use of alternate target materials having different characteristic X-rays.

Yet another feature the high dose output, through transmission target X-ray tube and methods of use is its ability to provide X-ray tube that requires no or limited heat dissipation in the form of air cooling or liquid cooling. Moreover, forced air cooling is thus more effective because of the increased surface area of the new anode configuration.

Yet another feature the high dose output, through transmission target X-ray tube and methods of use is its ability to provide an X-ray tube with increased longevity due to the large surface area anode target ability to dissipate heat.

Yet another feature of the high dose output, through transmission target X-ray tube and methods of use is its ability to provide a new structure and geometry for the anode to increase the surface area of the anode.

Yet another feature of the high dose output, through transmission target X-ray tube and methods of use is its ability to provide an anode configuration with better heat transfer characteristics which would enable the anode to operate at a lower temperature, and thus enable a lower melting point material choice with improved radiation output and extend the operational life of the X-ray tube.

Yet another feature of the high dose output, through transmission target X-ray tube and methods of use is its ability to provide a new structure and geometry for the cathode which deflects and/or accelerates the electrons toward a new structure and geometry for the anode.

Yet another feature of the high dose output, through transmission target X-ray tube and methods of use is its ability to provide a new structure and geometry for the filament which releases the electrons evenly distributed toward the a new structure and geometry for the anode.

Yet another feature of the high dose output, through transmission target X-ray tube and methods of use is its ability to provide minimal anode target to radiation sample distance resulting in an X-ray source which can be placed closer to a subject.

Yet another feature of the high dose output, through transmission target X-ray tube and methods of use is its ability to produces X-rays used for biological or organic material radiation, radiation treatment, treating certain diseases by killing or altering human cells, imaging, such as medical, industrial, and dual energy, non-destructive evaluation of objects, X-ray defection, X-ray diffraction patterns, therapeutic X-ray, analytical X-ray, and X-ray microscopy.

Yet another feature of the high dose output, through transmission target X-ray tube with a specifically coated hemispherical anode for therapeutic X-ray, X-ray defection, low power high dose application, medical imaging, industrial imaging, and dual energy imaging.

These and other features of high dose output, through transmission target X-ray tube and methods of use will become more apparent to one skilled in the art from the following Detailed Description of the exemplary Embodiments and Claims when read in light of the accompanying drawing Figures.

BRIEF DESCRIPTION OF THE DRAWINGS

The present high dose output, through transmission target X-ray tube and methods of use will be better understood by reading the Detailed Description of the exemplary embodiments with reference to the accompanying drawing figures, in which like reference numerals denote similar structure and refer to like elements throughout, and in which:

FIG. 3 is a graphical representation of the X-ray energy keV verses the dose for gold target;

FIG. 3.1 is a graphical representation of the X-ray energy keV verses the dose for a combination of materials such as Tungsten, Iridium, and Gold as the target;

It is to be noted that the drawings presented are intended solely for the purpose of illustration and that they are, therefore, neither desired nor intended to limit the disclosure to any or all of the exact details of construction shown, except insofar as they may be deemed essential to the claimed invention.

DETAILED DESCRIPTION

In describing the exemplary embodiments of the present disclosure, as illustrated in FIGS. 1-9 specific terminology is employed for the sake of clarity. The present disclosure, however, is not intended to be limited to the specific terminology so selected, and it is to be understood that each specific element includes all technical equivalents that operate in a similar manner to accomplish similar functions. The examples set forth herein are non-limiting examples, and are merely examples among other possible examples.

Figure 1:
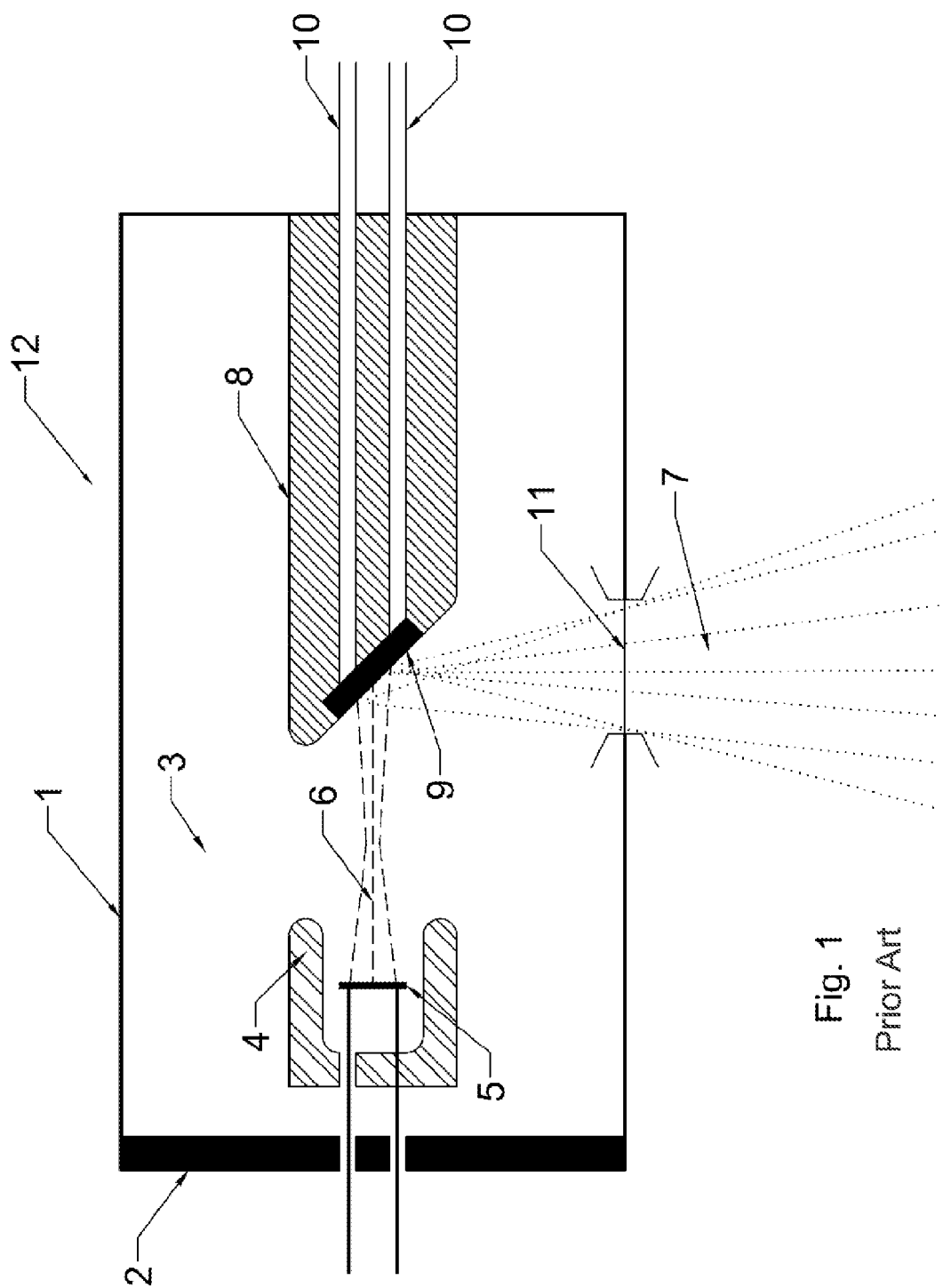
FIG. 1 is a schematic, cross sectional representation of a Coolidge type prior art X-ray tube.

Referring now to FIG. 1 there is illustrated a schematic cross sectional representation of Coolidge type X-ray tubes 12, shown in FIG. 1, includes X-ray tube housing 1, which may be glass or metal, high voltage insulation 2, and a vacuum dielectric 3 contained therein X-ray tube housing 1. In a Coolidge tube X-ray photons, shown as a fanned output radiation pattern 7, are generated by impinging an electron beam emanating from filament 5, shown as electron trajectory 6 onto the surface of a target anode 9, shown as X-ray target 9. Coolidge tubes may be operated single ended with the cathode, shown as cathode assembly 4, at a negative potential and anode 9 at ground, or double ended with the cathode 4 at a negative potential and the anode 9 at a positive potential. In either configuration the energy of acceleration is the difference between the electrode potentials. In a Coolidge tube X-ray the target anode 9 is fabricated from a heavy metal such as tungsten, tantalum or iridium and such materials are selected because of their density (tungsten-19.35, tantalum-16.65 or iridium-22.4 gr/cm3 (grams per cubic centimeter)) and high melting point (tungsten-3410, tantalum-2996 or iridium-2410 Celsius (C)). The material of the target anode 9 is most often mounted onto a thermally conductive material such as copper, shown as anode heat conductor 8. Furthermore in Coolidge type X-ray tubes 12 designs the amount of electrical energy between the electrode potentials to produce a given resulting radiation 7 is very high, resulting in heating of the target anode 9 material requiring special target cooling considerations such as a rotating target anode 9, air cooling or liquid cooling of the target anode 9, such as either by water or a dielectric oil flowing through cooling lines 10. The objective of cooling the anode assembly is to enable higher power operation of the X-ray tube.

Moreover, the target anode 9 is placed in line with the electron beam 6 and the resulting radiation 7 is emitted at right angles to the electron beam 6 through output radiation window 11 forming a beam of output radiation 7.

Figure 2:
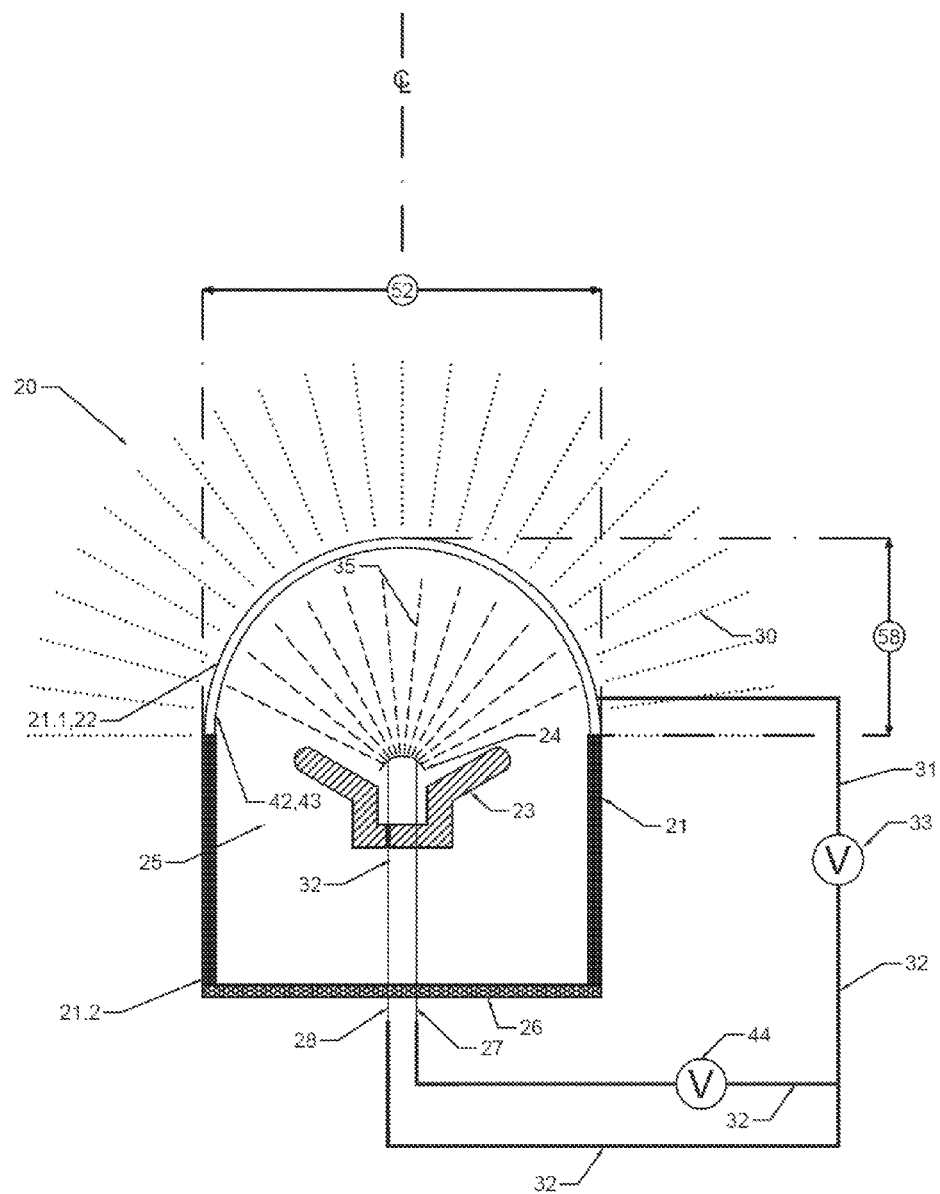
FIG. 2 is a schematic, cross sectional representation of an exemplary embodiment of a through transmission target X-ray tube showing a profile of electron trajectory lines which are being emitted from the cathode filament and showing a profile of the output radiation being emitted from the anode target.

Referring now to FIG. 2, by way of example, and not limitation, there is illustrated schematic cross sectional representation of an exemplary embodiment of high dose output, through transmission target X-ray tube 20. Preferably, through transmission target X-ray tube 20 includes evacuated sealed chamber or envelope, such as housing 21, which may be glass, alloy or metal, which creates evacuated space 25. One end, a first end 21.1 of housing 21 is preferably connected to first connector 31 of high voltage power supply 33. Contained within housing 21 preferably are primary elements anode structure 22, cathode structure 23, first filament lead 27, second filament leads 28, and filament 24. Moreover, anode structure 22 preferably includes target element or target material, such as through transmission target 43 anode as part of anode structure 22, where target is preferably deposited thereon inner surface 42 of first end 21.1 of housing 21. Cathode structure 23 may be connected to ground or second connector 32 of high voltage power supply 33. Filament 24 preferably is connected to first filament lead 27 of heating current power supply 44 and second filament leads 28 of heating current power supply 44. Preferably target 43 being the electron interacting material deposited thereon inner surface 42 of first end 21.1 of housing 21 and together with arcing or circular cross-sectional, dome or hemispherical shaped first end 21.1 of housing 21 comprise anode structure 22. Yet still further contained within housing 21 preferably is high voltage insulator 26 partially enclosed housing 21 thereon second end 21.2 of housing 21.

Combination of bremsstrahlung and characteristic radiation 30 is preferably emitted from through transmission target X-ray tube 20 in arcing or half circular cross-sectional, dome or hemispherical shape radiation pattern. Characteristic radiation is produced when an energetic electron emanates from heated filament 24 and is accelerated by high voltage power supply 33, the electrical energy between the electrode potentials of anode structure 22 and cathode structure 23 (cathode voltage) onto the surface of target anode structure 22, shown as electron trajectory 35 (plurality of accelerated electrons originating from said filament 24), knocks an electron from target element, such as target 43, out of its orbit. When this occurs an electron in the next higher energy orbit will fall into this lower energy orbit and give off a burst of radiation equivalent to the energy difference between the two electron orbits. Because each element or material of target 43, has a different atomic structure, energy level of the emitted radiation is unique and characteristic of that element. The atomic levels are designated K, L, M, N . . . and each level has additional sub-levels designated α, β . . . . For example, if there is a vacancy in the K-orbit of an element, target 43, and an electron drops from the L orbit to fill the vacancy then the energy given off is equal to $E_{x-ray}=E_{k\alpha}-E_L$. The predominated and most useful characteristic radiation is the $K_\alpha$ (k alpha) energy level of the various elements, target 43, and occur at energies less than 100 kilovolts (kV) for high voltage power supply 33, the electrical energy between the electrode potentials of anode structure 22 and cathode structure 23. It is recognized herein that through transmission target X-ray tube 20 preferably may use the Kα characteristic radiation of target 43 or a composite target 43 composed of various elements to fill in the X-ray spectrum below 100 kilovolts (kV) and bremsstrahlung from higher Z elements to produce an X-ray tube of superior performance characteristics.

TABLE I target 43 element, material or combinations thereof

| Anode Material(43) | Bremsstrahlung Radiation | Characteristic Radiation | Total Radiation |
| --- | --- | --- | --- |
| Tungsten | 700 | 300 | 1000 |
| Tungsten + Gold | 700 | 600 | 1300 |
| Tungsten + Gold + Iridium | 700 | 900 | 1600 |

All readings normalized for a Tungsten anode and operation at 200 kV.

It is recognized herein that target 43 is preferably formed thereon anode structure 22 via electro-chemically platted, mechanically bonded, or vapor deposited using evaporation or sputtering technique.

It is recognized herein that high voltage power supply 33, the electrical energy between the electrode potentials of anode structure 22 and cathode structure 23 produces an electrostatic field, such as electron trajectory 35 (plurality of accelerated electrons originating from said filament 24) that equally distributes said plurality of accelerated electrons originating from said filament onto said at least one element formed on said anode structure.

A New Housing and Target Anode Structure Shape

To address the shortcomings of traditional X-ray tubes and current through transmission tubes through transmission target X-ray tube 20 with selective anode structure 22 elements has been designed. Preferably, through transmission target X-ray tube 20 utilizes a large diameter 52, hemispherical shaped structure for anode structure 22 of housing 21 formed of a low Z material, such as aluminum or beryllium, for a substrate onto which various target 43 elements or material may be deposited to form anode structure 22. A hemispherically shaped anode structure 22 is preferably used because it has twice the surface area of a disk shaped substrate of the same diameter. The area of a hemisphere is $2\pi r^2$ and the area of a disk is $\pi r^2$. This increase in surface area allows for increased power dissipation, improved electron symmetry across target 43, increased surface area to dissipate heat, and thus, improved cooling efficiency. Moreover, the anode substrate 22 may be coated with various elements, combination of elements or their alloys as target 43 to form anode structure 22 and produce desirable characteristic symmetrical hemispherical shaped x-ray field, such as radiation 30 (output x-ray spectrum) for specific purposes or high Z elements to produce increased output with a combination of bremsstrahlung and characteristic radiation 30. This is all accomplished at reduced cathode potential, high voltage power supply 33, for the same radiation 30 output as compared to a Coolidge type X-ray tube, shown in FIG. 1.

It is recognized herein that the hemispherical shaped anode structure 22 configured with a large surface area results in a self-cooled or cooler or lower temperature anode due to its ability to dissipate heat across a larger surface area, and thus, does not require any internal cooling system, such as rotating anode or cooling fluids with internal passages, to dissipate the heat generated in anode structure 22 during operation.

It is further recognized herein that the hemispherical shaped anode structure 22 configured with a large surface area provides equalized distribution of electrons symmetrically across anode structure 22 and thus, generates an even distribution of radiation 30.

Specifically Coated Target Anode Substrate

Preferably, through transmission target X-ray tube 20 utilizes Gold as target 43 coated hemispherical anode structure 22 deposited on inner surface 42 of first end 21.1 of housing 21 to form anode structure 22. Gold as target 43 element of anode structure 22 has a $K\alpha$ peak at approximately 68.8 keV and $K_\beta$ peak at approximately 77 keV when operated at 150 to 160 kilovolts (kV), high voltage power supply 33, the bremsstrahlung and characteristic radiation spectrum, radiation 30, as shown in FIG. 3, is ideally suited for high output irradiation application(s) and is far superior to traditional X-ray tubes, such as Coolidge type X-ray tube, shown in FIG. 1. because of the following advantages. Preferably Gold target 43 element of anode structure 22 provides the following advantages due to the efficiency of radiation 30 produce is proportional to the atomic number of Gold target 43 of anode structure 22 multiplied by the kV of high voltage power supply 33. Here, the atomic number of Gold (Au) is 79 the atomic number of Tungsten (W) is 74 for Coolidge type X-ray tube, shown in FIG. 1. The percent difference between the two atomic numbers is 6.75%. Based on formula for calculating radiation 30 $1-((kV*z)/(kV*z))*100=$Efficiency $kV*Z*10-6$; Gold utilized as target anode structure 22 is 6.75% more efficient (conversion efficiency) in generating bremsstrahlung radiation, radiation 30, at the same kilovolts (kV) levels as Tungsten (W) targets 43 for Coolidge type X-ray tube, shown in FIG. 1. Traditional X-ray tubes cannot take advantage of using Gold as target 43 material for high power irradiation tubes because of the lower melting temperature of Gold (1064 Celsius) compared with Tungsten (3422 Celsius) due to the small surface area design of anode 8 of Coolidge type X-ray tube, shown in FIG. 1. However, with the larger target 43 area provided for by hemispherical shaped structure of anode structure 22 of through transmission target X-ray tube 20 the anode surface area 22 is increased allowing for increased power dissipation; and therefore, lower melting point elements, such as Gold, may be utilized for target 43. For example, anode structure 22 area can be as large as 25 square inches compared to 1 square inch for anode 9 of FIG. 1 which may operate at 1 Mega $W/cm^2$. It is contemplated herein that other lower melting point elements for target 43, such as elements with atomic number between 74 through 82, and more specifically Lead (Pb) and Uranium (U) and the like may be utilized as target 43 material for anode structure 22. It is further contemplated herein that between 4-40 microns thickness for target 43 material (target element thickness) for anode structure 22 is preferred and the thickness of target 43 material is chosen depending on the material selected for target 43, desired type of radiation 30 emission, and the accelerating voltage of high voltage power supply 33. These characteristics enable monochromatic beams with increased radiation at lower kV of high voltage power supply 33.

Target 43 is preferably formed of a suitable material, such as gold (Au) or Lead (Pb), including other elements with atomic number between 74 through 82, and additionally copper (Cu), silver (Ag), and Uranium (U) may be utilized for target anode structure 22. Preferably, these materials include other suitable characteristics, such as high $K_\alpha$ energy level, high conversion rate of electrons to X-ray or other beneficial characteristic understood by one skilled in the art.

Furthermore, filament 24 of through transmission target X-ray tube 20 is preferably configured in an arcing or circular cross-sectional or hemispherical shaped configuration, positioned therein cathode structure 23 and such configuration electrostatically focuses electron beam 29 along electron trajectory 35 toward anode structure 22 or more specifically in a one-hundred and eighty degree (180°) or hemispherical shaped pattern onto target 43 of anode structure 22 to evenly distribute electron beam 29 across target 43, inner surface 42 of first end 21.1 of anode structure 22 of housing 21. Moreover filament 24 is preferably coated with an oxide material approximately 40-50 microns thick and indirectly heated using a nicon wire connected to first filament lead 27 of heating current power supply 44 and second filament leads 28 of heating current power supply 44 to heat filament 24 to provide thermal vibration energy to free electrons from filament 24. Such distribution of electron beam 29 across target 43 and anode structure 22 lowers or reduces the watt density (Watts/Area, $W/cm^2$) loading of target 43 and anode structure 22, as set forth above, and, thus prevents hot spots due to even heating of target 43 and anode structure 22.

It is recognized herein that the hemispherical shaped anode structure 22 and arcing or hemispherical shaped filament 24, in combination, provides equalized distribution of electrons symmetrically across target 43 and anode structure 22.

It is further recognized herein that the hemispherical shaped anode structure 22 and arcing or hemispherical shaped filament 24, in combination, provides collimating electron trajectory 35 across target 43 and anode structure 22.

It is further recognized herein that the hemispherical shaped anode structure 22 and arcing or hemispherical shaped filament 24, in combination, provides equalized electron travel distance 58, the distance electron beam 29 travels from filament 24 to target anode structure 22.

It is further recognized herein that the hemispherical shaped anode structure 22 is preferably formed of a material that is substantially X-ray transparent, such as Beryllium, Carbon, Aluminum, Ceramic, Stainless Steel, alloys of said material and combinations thereof.

Still furthermore, cathode structure 23 of through transmission target X-ray tube 20 is preferably configured in an 'V' shape or notched 'V' shape cross-section, or bowl or flared configuration or the like and such configuration electrostatically directs electron beam 29 efficiently and equally distributed along electron trajectory 35 toward target 43 and anode structure 22 or more specifically in a one-hundred and eighty degree (180°) pattern onto target 43 and anode structure 22 to evenly distribute electron beam across hemispherically shaped target 43 and anode structure 22, inner surface 42 of first end 21.1 of housing 21.

It is recognized herein that the hemispherical shaped anode structure 22, arcing or hemispherical shaped filament 24, and flared cathode structure 23 in combination, provides maximum generation of directional X-rays proximately symmetrical about center line CL.

It is recognized herein that the transmission type X ray tube 20 target may include an anode structure having a specifically coated target 43, such as by using parameters of target 43 material.

It is recognized herein that through transmission target X-ray tube 20 may include a specifically coated target 43 of anode structure 22 for X-ray defection, such as by using low Z materials for target 43.

It is recognized herein that through transmission target X-ray tube 20 may include a specifically coated target 43 of anode structure 22 for X-ray deflection, such as by using high Z materials for target 43.

It is recognized herein that through transmission target X-ray tube 20 may include a specifically coated target 43 of anode structure 22 for low power requirements of high voltage power supply 33, or for high dose radiation 30 application, such as by using parameters of the target 43 material.

It is recognized herein that through transmission target X-ray tube 20 may include a specifically coated target 43 of anode structure 22 for medical imaging, such as by using Molybdenum as target 43 material.

It is recognized herein that through transmission target X-ray tube 20 may include a specifically coated target 43 of anode structure 22 for industrial imaging, such as by using Gold as the target material 43 to increase the number of X-ray photons which in turn improves image contrast.

Referring now to FIG. 3, by way of example, and not limitation, there is illustrated graphical representation of the X-ray energy keV($\lambda$) verses output radiation dose for through transmission target X-ray tube 20, shown having target 43 material of Gold. In this graph of the characteristic radiation R1 (k alpha energy line) of target 43 material of Gold the Y axis represents dose a given quantity of output radiation, radiation 30, in photons, such as number of photons and the X axis represents Kilovolts (wavelength) a given quantity of X-ray energy, and as Kilovolts (wavelength) changes so does the number of photons dose represented by the graph for Gold. As seen in the graph radiation spikes occur and are designated as $K_\alpha$ and $K_\beta$ dose peaks, which are characteristic radiation peaks that results from using target 43 material of Gold. Using target 43 material of Gold results in increases in radiation dose occur for target 43 material without requiring increased input power kV($\lambda$), due to radiation spikes shown as proximately kV($\lambda$) of 68.7 corresponding to $K_\alpha$ peak and kV($\lambda$) of 77 corresponding to $K_\beta$ peak.

Referring now to FIG. 3.1, by way of example, and not limitation, there is illustrated graphical representation of the X-ray energy kV($\lambda$) verses output radiation dose for through transmission target X-ray tube 20, shown having target 43 material of configured based on a combination of materials for target 43. Preferably target 43 is preferably formed of a suitable material, such as gold (Au), Lead (Pb), including other elements with atomic number between 74 through 82, and additionally copper (Cu), silver (Ag), and Uranium (U). In this graph of the characteristic radiation R2 of combination target 43 of Gold Tungsten and Iridium the Y axis represents dose a given quantity of radiation in photons, such as number of photons and the X axis represents Kilovolts (wavelength) a given quantity of X-ray energy, and as Kilovolts (wavelength) changes so does the number of photons dose. As seen in the graph radiation spikes occur and are designated as $K_\alpha$ and $K_\beta$ peaks for both Gold Tungsten and Iridium, which are characteristic radiation peaks that results from using combination of materials for target 43. Using target 43 material of Gold Tungsten and Iridium results in increases in output radiation dose, radiation 30, which occur for combination material, target 43 without requiring increased input power kV($\lambda$) high voltage power supply 33, as shown in Table II

TABLE II

| Element | $K_\alpha 1$ | $K_\alpha 2$ | $K_\beta 1$ | $K_\beta 2$ |
|---|---|---|---|---|
| Gold | 68.804 | 66.990 | 77.985 | 80.182 |
| Tungsten | 59.318 | 57.982 | 67.244 | 69.1 |
| Iridium | 64.896 | 63.287 | 73.560 | 75.620 |

It is recognized herein that for each material selected from the element list above to make up combination material, for target 43, as shown the characteristic radiation R2 of target 43 will have additional and different $K_\alpha$ and $K_\beta$, peaks for each material selected and added to target 43. It is further recognized herein that the addition of each material selected from the list above results in target 43 material based on a plurality of materials and each material generates additional and different $K_\alpha$ and $K_\beta$, peaks, and thus increases in output radiation dose, radiation 30, occur for combination material, target 43 without requiring increased input power kV($\lambda$), high voltage power supply 33, as shown by the increase in area of the graph of the characteristic radiation R2. By adding a plurality of combination material listed above for target 43 the improved output radiation dose, radiation 30, occurring for combination material target 43 will be greatly increased. If 1000 watts of power generates a dose of 100 Gray then a combination target 43 may generate 50% more dose.

It is still further recognized that increases in output radiation dose, radiation 30, for target 43 material based on the above list of materials without requiring increased input power (kV($\lambda$)*mA) reduces cooling requirements.

It is still further recognized that increases in output radiation dose, radiation 30, for target 43 material based on the above list of materials without requiring increased input power (kV($\lambda$)*mA), high voltage power supply 33, enables radiation and irradiation applications at lower input power (kV($\lambda$)*mA), such as medical applications.

Figure 4:
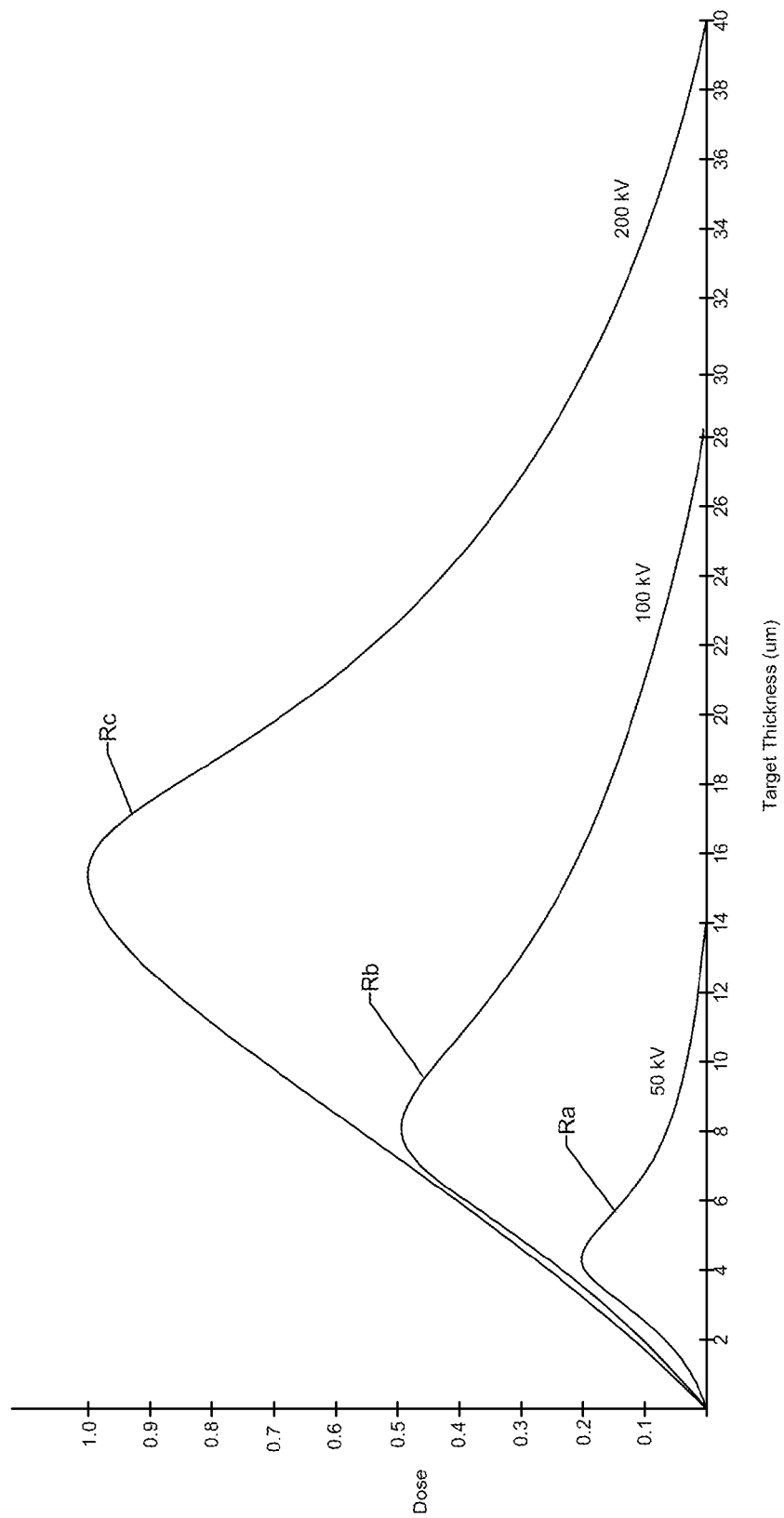
FIG. 4 is a graphical representation of the target anode thickness verses dose for different kV.

Referring now to FIG. 4, by way of example, and not limitation, there is illustrated a graphical representation of the target 43 material empirically determined thickness verses dose output radiation, radiation 30, for through transmission target X-ray tube 20. In this graph of the Bremsstrahlung radiation of target 43 verses material thickness the Y axis represents dose a given quantity of output radiation, radiation 30, in photons, such as number of photons and the X axis represents target 43 material thickness in micrometers, and as target 43 material thickness changes so does the number of photons represented by the graph. Thee representative curves are presented for varying high voltage power supply 33, the electrical energy between the electrode potentials of anode structure 22 and cathode structure 23, such as 50 kV Ra, 100 kV Rb, and 200 kV Rc (k alpha energy lines). In each curve dose ramps up, plateaus, and tapers off based on increased target 43 material thickness. It is recognized herein FIG. 4 that approximately 4-40 microns thickness for target 43 material for target anode structure 22 is preferred, and more preferred approximately 4-18 microns thickness for target 43 material for target anode structure 22, and the thickness of target 43 material is chosen depending on the material selected, desired type of radiation 30 emission, and the accelerating voltage of high voltage power supply 33.

It is further recognized herein FIG. 4 that the higher the accelerating voltage, high voltage power supply 33, the more efficient through transmission target X-ray tube 20 is at converting electrons emitted by filament 24 into increased dose output radiation 30 to take advantage of the characteristic radiation peeks.

It is still further recognized herein FIG. 4 that no sharp points occur in the characteristic radiation R curves 50 kV Ra, 100 kV Rb, and 200 kV Rc, (k alpha energy line) and more specifically representative radiation R curve 50 kV Ra having a plateau from approximately 3-5 microns thickness of target 43, representative radiation R curve 100 kV Rb having a plateau from approximately 7-10 microns thickness of target 43, representative radiation R curve 200 kV Rc having a plateau from approximately 14-18 microns thickness of target 43 and collectively representative radiation R curves 50 kV Ra, 100 kV Rb, and 200 kV Rc plateau from preferred 4-18 microns thickness of target 43.

Design variables of through transmission target X-ray tube 20, such as material to be selected for target 43 (material having Z from 73 to 79 heavier elements), selected target 43 material thickness in microns, and selected voltage of high voltage power supply 33 changes the dose output radiation 30, such as increased dose output radiation at lower high voltage power supply 33 power.

It is still further recognized herein FIG. 4 that changes to selected target 43 material and/or selected target 43 material thickness in microns changes dose output radiation 30.

It is still further recognized herein FIG. 4 that dual energy through transmission target X-ray tube 20 having high voltage power supply 33 operational at two voltages of for example 50 kV and 100 kV, may preferably select target 43 material thickness to accommodate both energies, for example, target 43 material thickness of between 3-10 microns may be selected where representative radiation R curve 50 kV Ra having plateau from approximately 3-5 microns thickness of target 43 (50 kV) and representative radiation R curve 100 kV Rb having plateau from approximately 7-10 microns thickness of target 43 (100 kV) overlap.

Figure 5:
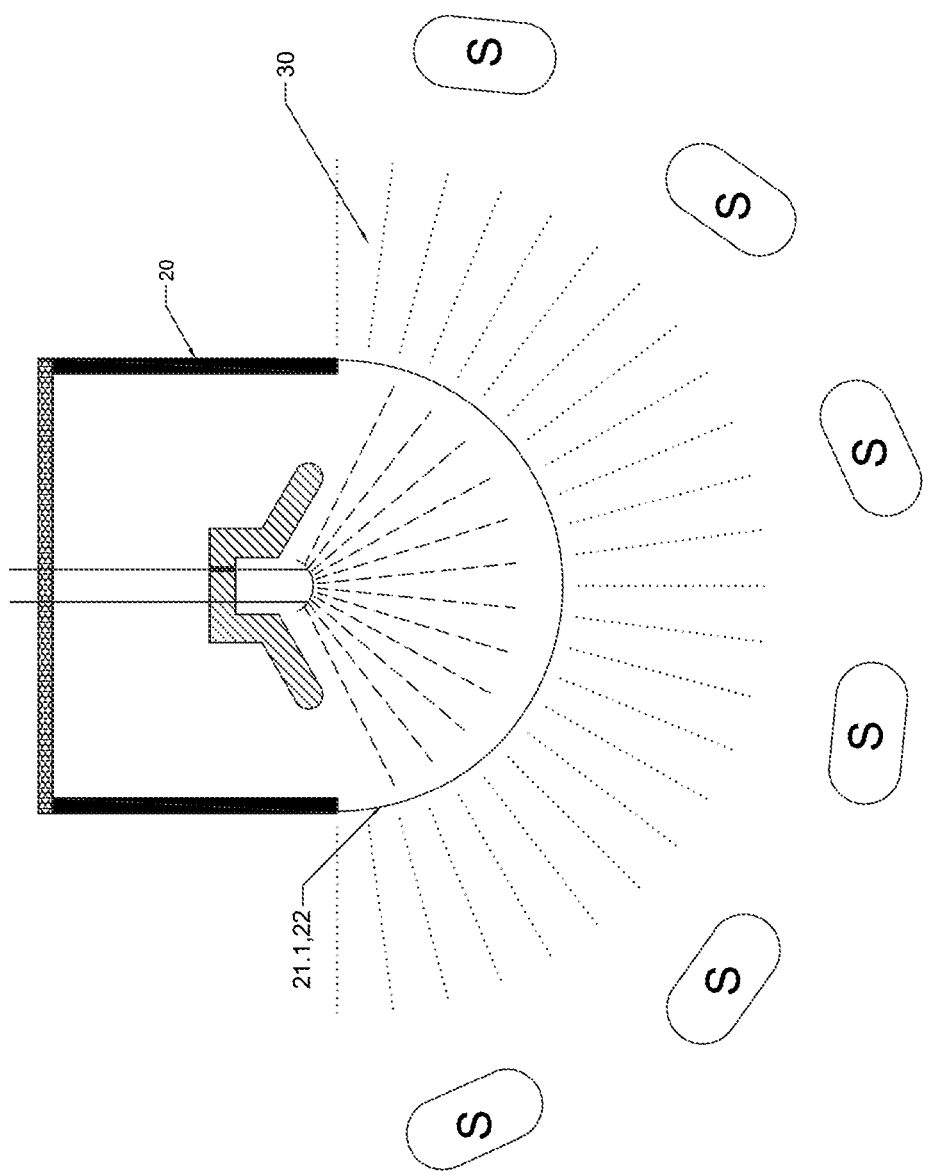
FIG. 5 is a diagram representation of an example application to radiate biological material utilizing the through transmission target X-ray tube of FIG. 2.

Referring now to FIG. 5, by way of example, and not limitation, there is illustrated an example application to radiate biological material utilizing through transmission target X-ray tube 20, as shown and described in FIG. 2. In use, through transmission target X-ray tube 20 characteristic and Bremsstrahlung radiation 30 is preferably emitted from through transmission target X-ray tube 20 in arcing or half circular cross-sectional, dome or hemispherical shape radiation 30 pattern. Preferably, through transmission target X-ray tube 20 produces characteristic radiation 30 configured to enable a large area of intense radiation 30 to improve throughput radiation and radiate more or an increased number of samples S simultaneously. Furthermore, samples S may be positioned proximate or adjacent anode structure 22 of housing 21 of through transmission target X-ray tube 20, either positioned stationary or via a mobile mechanical structure depending on the application for an added level of even exposure of samples S subjected to characteristic radiation 30 by taking advantage of the geometrical shape of the radiation pattern. Moreover, through transmission target X-ray tube 20 preferably produces a symmetrical radiation field, radiation 30, around first end 21.1 of through transmission target X-ray tube 20 to provide a consistent dose of radiation 30 to all areas of samples S.

It is recognized herein that through transmission target X-ray tube 20 radiation 30 output is increased over Coolidge type prior art X-ray tube, shown in FIG. 1. For example, if two times radiation 30 output from through transmission target X-ray tube 20 then samples S require half the necessary runtime of through transmission target X-ray tube 20, and additionally higher dose radiation 30 using less power requirements for high voltage power supply 33, lowered heat load in BTU of air conditioning load savings with lowered power requirements, high voltage power supply 33, all results in lowered operating costs of through transmission target X-ray tube 20. Moreover, hemispherical shaped anode structure 22 configured with a large surface area results in a cooled or cooler or lower temperature anode due to its ability to dissipate heat, and thus, does not require any internal or external cooling system, such as rotating anode or cooling fluids with internal passages, to dissipate the heat generated in anode structure 22 during operation, and, thus reduces the operating cost of through transmission target X-ray tube 20.

Figure 6:
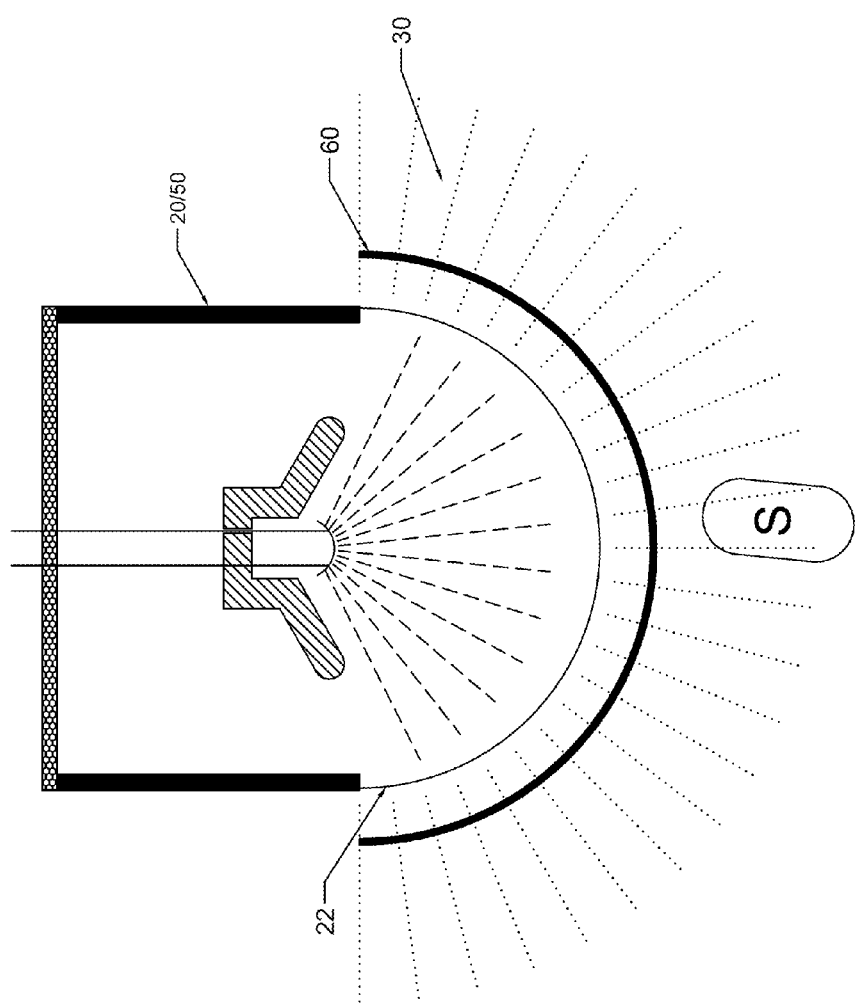
FIG. 6 is a schematic, elevational, cross sectional representation of an exemplary embodiment of the through transmission target X-ray tube of FIG. 2 in combination with a monochromatic filter.

Referring now to FIG. 6, by way of example, and not limitation, there is illustrated schematic cross sectional representation of high dose output, through transmission target X-ray tube 20 (alternatively 50) in combination with monochromatic filter 60. Preferably, monochromatic filter 60 may be positioned proximate or adjacent first end 21.1 of housing 21 in the path of radiation 30 or between anode structure 22 of housing 21 and samples S in the path of radiation 30 to attenuate or filter selected radiation from radiation 30. Referring again to FIG. 3 by way of example, and not limitation, monochromatic filter 60 may be configured to filter or attenuate a specified radiation 30 (monochromatic output x-ray spectrum), such as all radiation less than kV($\lambda$) of 54 to produce specified radiation 30 of $K_\alpha$ and $K_\beta$ dose peaks, which are characteristic radiation peaks that results from using target 43 material of Gold.

It is contemplated herein that to produce a monochromatic output X-ray spectrum through transmission target X-ray tube 20 (alternatively 50) may utilize monochromatic filter 60 to filter output X-ray spectrum, such as radiation 30 just below a K$\alpha$ energy of target 43.

It is contemplated herein that to produce a monochromatic output X-ray spectrum through transmission target X-ray tube 20 (alternatively 50) may utilize adjusting said cathode voltage, high voltage power supply 33, the electrical energy between the electrode potentials of anode structure 22 and cathode structure 23, just above said K$\alpha$ energy of target 43.

It is contemplated herein that to produce a monochromatic output X-ray spectrum through transmission target X-ray tube 20 (alternatively 50) may utilize as a biological cell irradiator, a virus deactivation irradiator, an insect irradiator, and a food irradiator.

Figure 7:
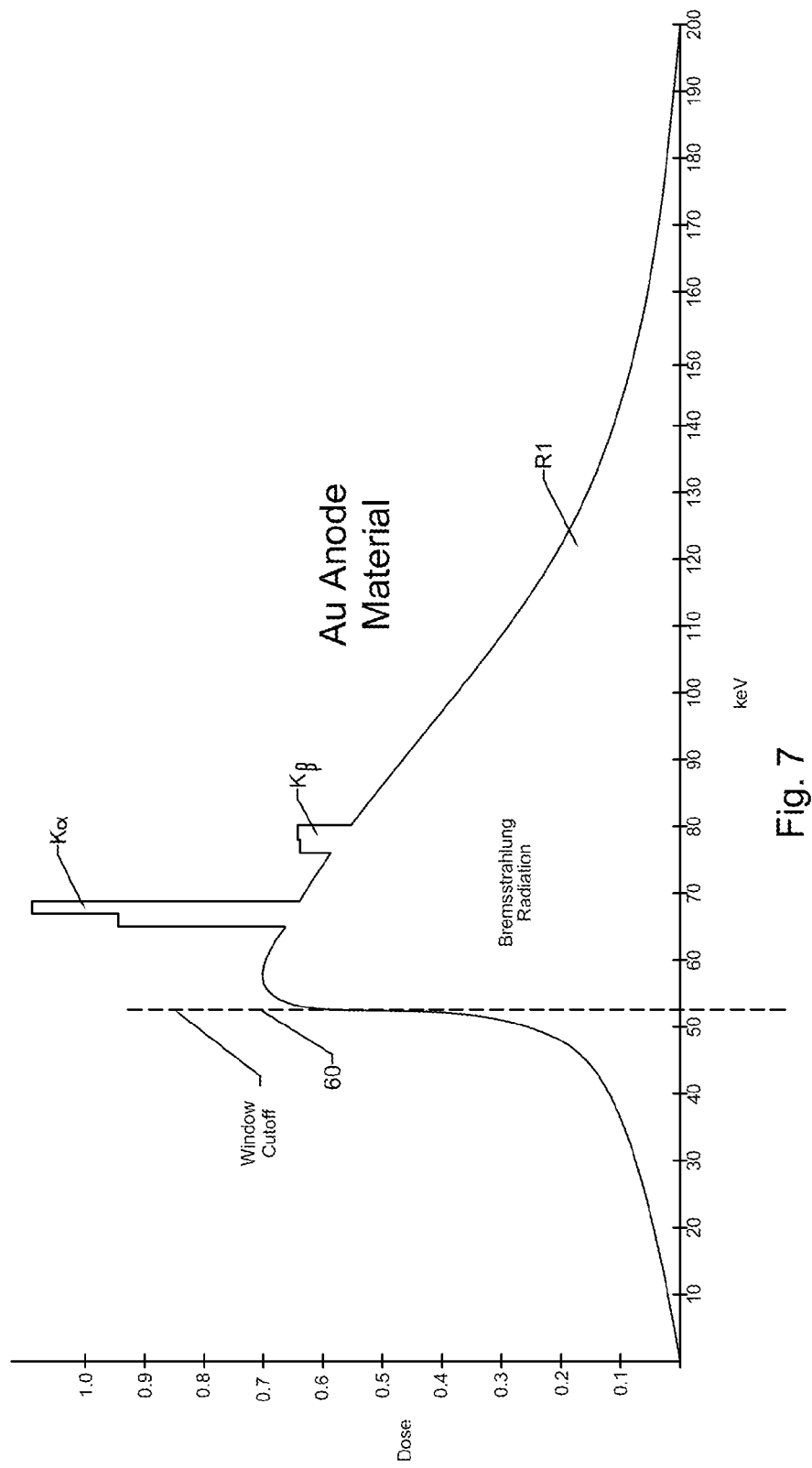
FIG. 7 is a graphical representation of the X-ray energy verses the dose the through transmission target X-ray tube in combination with a monochromatic filter of FIG. 6.

FIG. 7 is a graphical representation of the X-ray energy verses the dose the through transmission target X-ray tube 20 in combination with a monochromatic filter of FIG. 6. In this graph of the characteristic radiation R1 of target 43 material of Gold the Y axis represents dose a given quantity of output radiation 30 in photons, such as number of photons and the X axis represents Kilovolts (wavelength) a given quantity of X-ray energy, between kV(λ) of 75 and kV(λ) of 85, and as Kilovolts (wavelength) changes so does the number of photons represented by dose radiation 30 for Gold. As seen in the graph radiation spikes occur and are designated as $K_\alpha$ and $K_\beta$ dose peaks, which are characteristic radiation peaks that results from using target 43 material of Gold. In use, selected target 43 material and its $K_\alpha$ and $K_\beta$ dose peaks along with selected monochromatic filter 60 preferably enables a desired radiation profile for radiation 30, and, thus may be specified to achieve a variety of specific radiation 30 profiles for through transmission target X-ray tube 20 (alternatively 50) for specified imagery and therapy analysis, functions, examples or uses.

Figure 8:
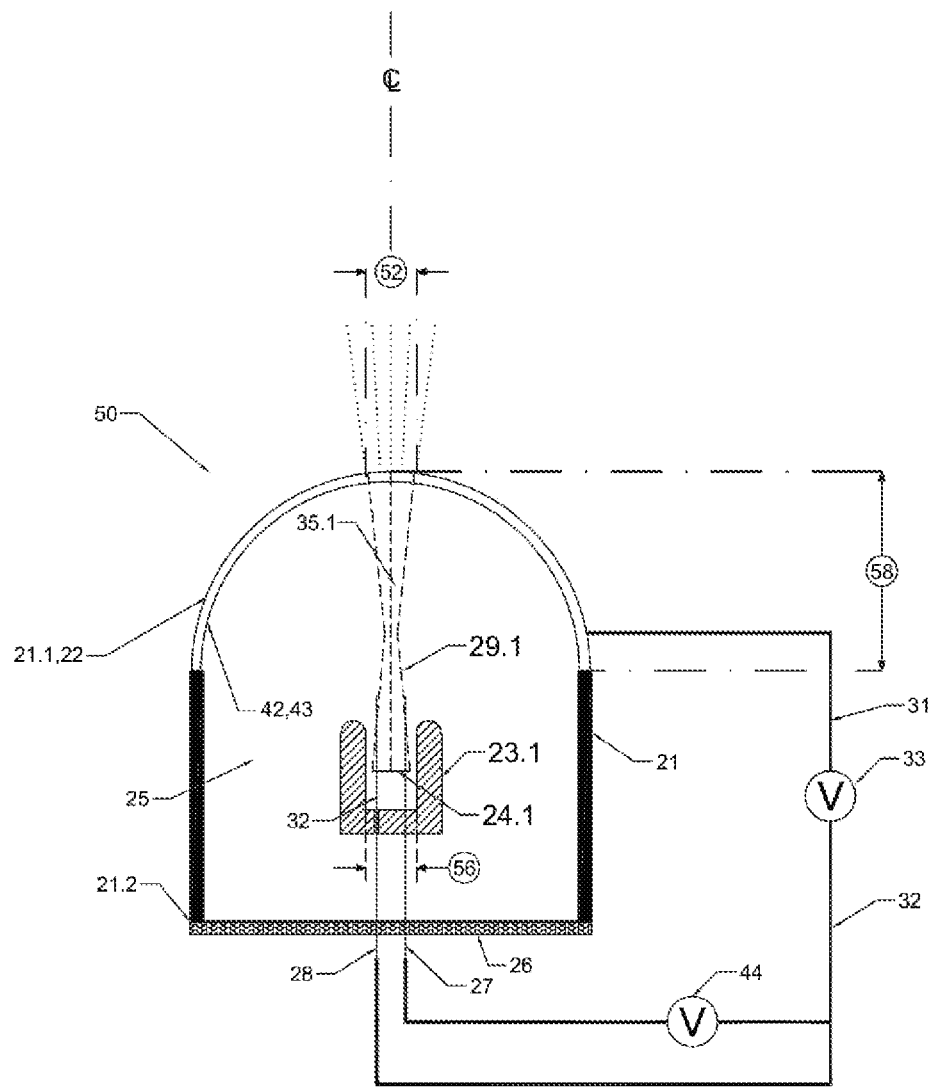
FIG. 8 is a schematic, elevational, cross sectional representation of an alternate exemplary embodiment of through transmission target X-ray tube showing a profile of electron trajectory lines which are being emitted from the cathode filament and showing a profile of the output radiation being emitted from the anode target.

Referring now to FIG. 8, by way of example, and not limitation, there is an illustrated schematic cross sectional representation of alternate exemplary embodiment of high dose output, through transmission target X-ray tube 50. Preferably, through transmission target X-ray tube 50 includes evacuated sealed chamber or envelope, such as housing 21, which may be glass, alloy or metal. One end, a first end 21.1 of housing 21 is preferably connected to first connector 31 of high voltage power supply 33. Contained within housing 21 preferably are primary elements anode structure 22, cathode structure 23.1, first filament lead 27, second filament leads 28, and filament 24.1. Moreover, anode structure 22 preferably includes through transmission target 43 anode as part of anode structure 22, wherein target 43 is preferably deposited thereon inner surface 42 of first end 21.1 of housing 21. Cathode structure 23.1 may be connected to ground or second connector 32 of high voltage power supply 33. Filament 24.1 preferably is connected to first filament lead 27 of heating current power supply 44 and second filament leads 28 of heating current power supply 44. Target 43 being the electron interacting material deposited thereon inner surface 42 of first end 21.1 of housing 21 and together with arcing or circular cross-sectional or hemispherical shaped first end 21.1 of housing 21 comprise anode structure 22. Yet still further contained within housing 21 preferably is high voltage insulator 26 partially enclosed housing 21 thereon second end 21.2 of housing 21.

Filament 24.1 of through transmission target X-ray tube 50 is preferably configured in a straight linear or slightly curved cross-sectional or planar or disc shaped configuration within cathode structure 23.1 and such configuration electrostatically focuses electron beam 29.1 along electron trajectory 35.1 toward target 43 and anode structure 22 or more specifically in a focused spot configuration pattern onto target 43 and anode structure 22 to concentrate electron beam 29.1 proximate center line CL across the inner surface 42 of first end 21.1 of housing 21.

Still furthermore, cathode structure 23.1 of through transmission target X-ray tube 50 is preferably configured in an 'U' shape cross-section, or cylinder configuration or other focusing, narrowing, or targeted configuration and such configuration electrostatically accelerate electron beam 29.1 along electron narrow trajectory 35.1 toward target 43 and anode structure 22 or more specifically in a focused pattern onto target 43 and anode structure 22 to narrowly distribute electron beam 29.1 across hemispherically shaped target 43 and anode structure 22, inner surface 42 of first end 21.1 of housing 21. Such concentration of electron beam 29.1 enables high dose output in narrow spot configuration having anode diameter 52, and through transmission target X-ray tube 50 may be utilized for applications, such as, to produce focused X-rays used for, radiation treatment, imaging, such as medical, industrial, and dual energy (dual output x-ray spectrum), non-destructive evaluation of objects.

It is contemplated herein that spot diameter 52 may be scaled up/down or increased or decreased in size based on design factors such as the opening or gap, such as inner diameter 56 of cathode structure 23.1, electron travel distance 58, of electron beam 29.1, the distance an electron travels from filament 24.1 to target 43 and anode structure 22, and/or diameter 52 of hemispherical shaped anode structure 22 for housing 21, as shown in FIG. 2. For example, in use, inner diameter 56 of cathode structure 23.1, electron travel distance 58 of electron beam 29.1 travels from filament 24.1 to target 43 and anode structure 22, and/or diameter 52 of hemispherical shaped anode structure 22 for housing 21 may be specified to achieve spot diameter 52 proportional to tumor sizes subject to radiation treatment depth of X-ray penetration.

It is recognized herein that the hemispherical shaped anode structure 22, filament 24.1, and narrowed cathode structure 23.1 in combination, provide focused, radially linearly symmetric X-ray field.

It is recognized herein that the hemispherical shaped anode structure 22, filament 24.1, and flared cathode structure 23.1 in combination, generate directional X-rays proximate center line CL for therapeutic X-ray treatment of melanoma and other cancer cells.

Figure 9:
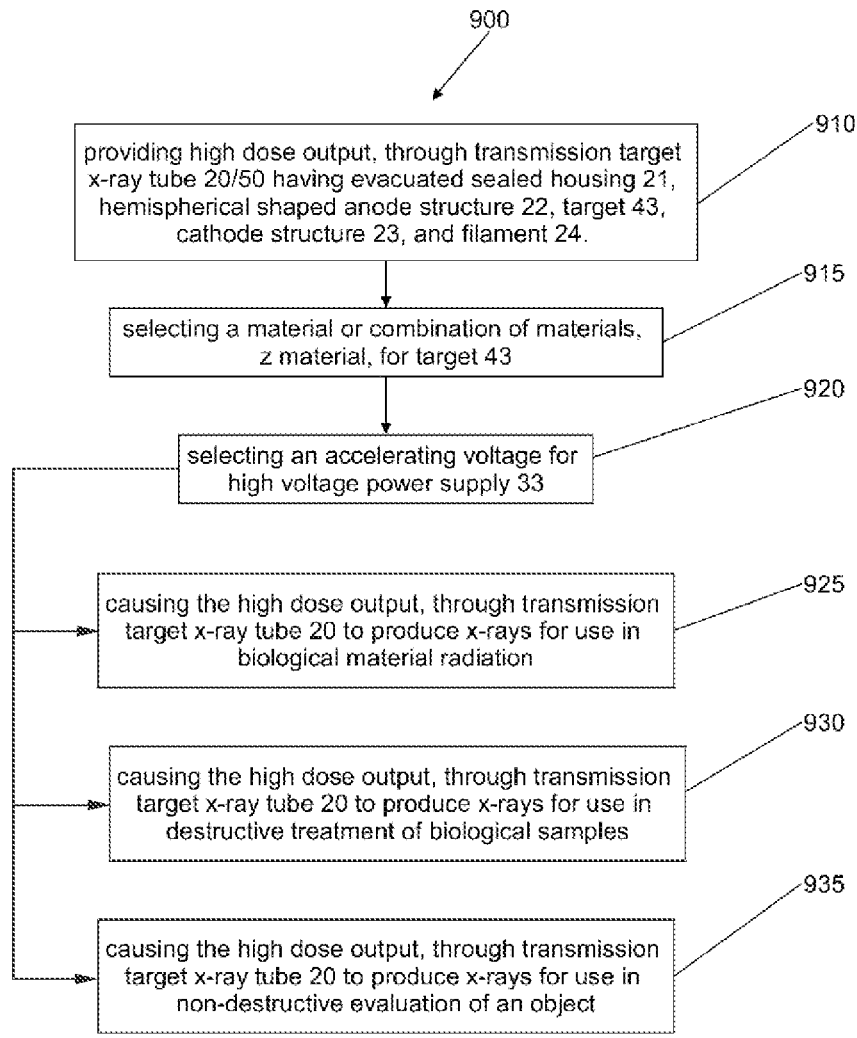
FIG. 9 is a flow diagram of a method of generating symmetrical shaped X-ray field.

It is contemplated herein that monochromatic filter 60 may be utilized with through transmission target X-ray tube 50 similar to that shown and disclosed in FIGS. 6 and 7. Referring now to FIG. 9, by way of example, and not limitation, there is illustrated a flow diagram 900 of a method of generating symmetrical hemispherical shaped X-ray field. In block or step 910, providing high dose output, through transmission target X-ray tube 20/50 having evacuated sealed housing 21, hemispherical shaped anode structure 22, cathode structure 23, target 43, and filament 24 as described herein. In block or step 915 selecting a material or combination of materials, z material, for target 43. In block or step 920 selecting an accelerating voltage for high voltage power supply 33. In block or step 925 causing the high dose output, through transmission target X-ray tube 20 to produce X-rays for use in biological material radiation. In block or step 930 causing the high dose output, through transmission target X-ray tube 20 to produce X-rays for use in non-destructive evaluation of an object. In block or step 935 causing the high dose output, through transmission target X-ray tube 20 to produce X-rays for use in destructive treatment of biological samples. Other treatments include imaging, such as medical, industrial, and dual energy, non-destructive evaluation of objects.

The foregoing description and drawings comprise illustrative embodiments of the present disclosure. Having thus described exemplary embodiments, it should be noted by those ordinarily skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one ordinarily skilled in the art to which this invention pertains having the benefit of the teachings presented in the foregoing descriptions and the associated drawings. Although specific terms may be employed herein, they are used in a generic and descriptive sense only and not for purposes of limitation. Moreover, the present invention has been described in detail; it should be understood that various changes, substitutions and alterations can be made thereto without departing from the spirit and scope of the invention as defined by the appended claims. Accordingly, the present invention is not limited to the specific embodiments illustrated herein, but is limited only by the following claims.

What is claimed is:

1. An X-ray tube for accelerating electrons under a high voltage potential, said X-ray tube comprising:
   an evacuated housing that is sealed;
   a through transmission target anode structure disposed on said housing, said anode structure configured in a hemispherical shape having a 2D base creating a circle with a center;
   a cathode structure disposed in said housing, said cathode structure configured to deflect the electrons toward said anode structure;
   a filament disposed in said housing, said filament positioned proximate the center of the circle created by the 2D base of the hemispherical shape, and between said anode structure and said cathode structure;
   wherein said cathode structure is positioned approximate said filament at the center of the circle created by the 2D base of the hemispherical shape of the anode structure; and
   wherein said evacuated housing is configured to vacuum seal therein said anode structure, said cathode structure, and said filament.

2. The X-ray tube of claim 1, wherein said anode structure is coated with at least one target element to produce a bremsstrahlung X-ray from a plurality of accelerated electrons originating from said filament.

3. The X-ray tube of claim 1, wherein said anode structure is formed of a material that is substantially X-ray transparent.

4. The X-ray tube of claim 2, wherein said at least one target element is formed thereon said anode structure via one of electro-chemically plating, mechanical bonding, or vapor deposition using evaporation or sputtering technique.

5. The X-ray tube of claim 3, wherein said material consists of one or more of the group consisting of: Beryllium, Carbon, Aluminum, Ceramic, Stainless Steel, or alloys thereof.

6. The X-ray tube of claim 2, wherein said cathode structure produces an electrostatic field that equally distributes said plurality of accelerated electrons originating from said filament onto said at least one element formed on said anode structure.

7. The X-ray tube of claim 6, wherein said X-ray tube produces a symmetrical hemispherical shaped X-ray field.

8. The X-ray tube of claim 4, wherein said at least one target element has a thickness between 2 and 50 microns.

9. The X-ray tube of claim 4, wherein said X-ray tube produces an output X-ray spectrum determined by said at least one target element and a cathode voltage.

10. The X-ray tube of claim 4, wherein said X-ray tube produces an output X-ray spectrum determined by a k alpha energy line of said at least one target element and a cathode voltage.

11. The X-ray tube of claim 8, wherein at least one target element thickness is determined by cathode voltage and a conversion efficiency of said at least one target element.

12. A method to produce a monochromatic output X-ray spectrum, said method comprising the steps of:
   providing an X-ray tube for accelerating electrons under a high voltage potential, said X-ray tube comprising:
      an evacuated housing that is sealed, a through transmission target anode structure disposed on said housing, said anode structure configured in a hemispherical shape having a 2D base creating a circle with a center, a cathode structure disposed in said housing, said cathode structure is configured to deflect the electrons toward said anode structure, a filament disposed in said housing, said filament positioned proximate the center of the circle created by the 2D base of the hemispherical shape and between said anode structure and said cathode structure, wherein said cathode structure is positioned approximate said filament at the center of the circle created by the 2D base of the hemispherical shape of the anode structure, and wherein said evacuated housing is configured to vacuum seal therein said anode structure, said cathode structure, and said filament,
   filtering said output X-ray spectrum just below a K alpha energy of said at least one target element; and
   adjusting said cathode voltage just above said K alpha energy of said at least one target element.

13. The method of claim 12, further comprising the step of producing levels of output X-ray spectrum with a known spectrum for use in analytical X-ray applications.

14. The method of claim 12, further comprising the step of producing a dual output X-ray spectrum for image analysis.

15. The method of claim 12, further comprising the step of producing a targeted output X-ray spectrum.

16. The method of claim 12, further comprising the step of producing high levels of output X-ray spectrum at a reduced cathode voltage by utilizing a k alpha line of selected said at least one target element.

17. The method of claim 12, further comprising the step of producing a targeted output X-ray spectrum for a biological cell irradiator.

18. The method of claim 12, further comprising the step of producing a targeted output X-ray spectrum for a virus deactivation irradiator.

19. The method of claim 12, further comprising the step of producing a targeted output X-ray spectrum for an insect irradiator.

20. The method of claim 12, further comprising the step of producing a targeted output X-ray spectrum for a food irradiator.

* * * * *